United States Patent [19]

Baudouin et al.

[11] 4,421,920

[45] Dec. 20, 1983

[54] PROCESS FOR THE PREPARATION OF 4-AMINO-CHLOROQUINOLINES

[75] Inventors: Michel Baudouin, St. Fons; Daniel Michelet, Tassin, both of France

[73] Assignee: Rhone-Poulenc Sante, Courbevoie, France

[21] Appl. No.: 339,722

[22] Filed: Jan. 15, 1982

[30] Foreign Application Priority Data

Jan. 16, 1981 [FR] France ................ 8100765

[51] Int. Cl.$^3$ ............... C07D 215/42; C07D 215/44; C07D 215/46
[52] U.S. Cl. .................. 546/163; 546/159; 546/160; 546/161; 546/162
[58] Field of Search ............ 546/159, 160, 161, 162, 546/163

[56] References Cited

U.S. PATENT DOCUMENTS 2,653,940 9/1953 Johnson .................. 546/159 X

OTHER PUBLICATIONS

Chem Systems, Inc., Chemical Abstracts, vol. 81, 3574y, (1974).

*Primary Examiner*—Diana G. Rivers
*Attorney, Agent, or Firm*—Stevens, Davis, Miller & Mosher

[57] ABSTRACT

4-Amino-chloroquinolines of the formula:

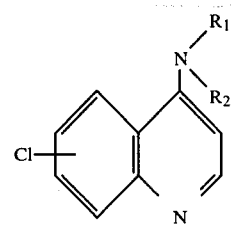

in which $R_1$ represents a hydrogen atom or an alkyl radical (1 to 5 carbon atoms), and $R_2$ represents an alkyl radical (1 to 5 carbon atoms) optionally substituted by a dialkylamino group, or a phenyl radical optionally substituted by one or more carboxy and hydroxy radicals and alkyl radicals (1 to 4 carbon atoms) optionally substituted by a dialkylamino group, are prepared by the condensation of an amine of the formula:

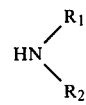

with a chloro-1,2,3,4-tetrahydroquinolin-4-one of the formula:

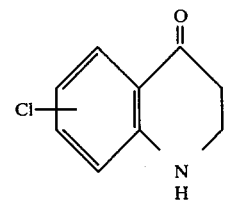

with aromatization of the tetrahydroquinoline, the reaction being carried out in the presence of a ruthenium based catalyst on a support.

The 4-amino-chloroquinoline products are useful as pharmaceuticals.

11 Claims, No Drawings

PROCESS FOR THE PREPARATION OF 4-AMINO-CHLOROQUINOLINES

The present invention relates to a process for the preparation of a 4-amino-chloroquinoline of the general formula:

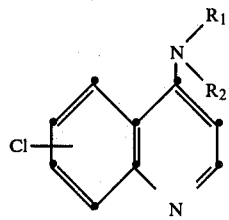

in which $R_1$ represents a hydrogen atom or an alkyl radical containing 1 to 5 carbon atoms and $R_2$ represents an alkyl radical containing 1 to 5 carbon atoms, which is optionally substituted by a dialkylamino group of which each alkyl radical contains 1 to 4 carbon atoms (for example the 4-diethylamino-1-methylbutyl group), or a phenyl radical optionally substituted by one or more radicals selected from the carboxy and hydroxy radicals and alkyl radicals containing 1 to 4 carbon atoms optionally substituted by a dialkylamino group of which each alkyl radical contains 1 to 4 carbon atoms (for example the 2-carboxyphenyl or 3-diethylaminomethyl-4-hydroxyphenyl group), from the corresponding chloro-1,2,3,4-tetrahydroquinolin-4-one of the general formula:

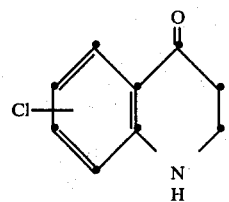

The products of the general formula (I) in which the chlorine atom is in the 7-position, $R_1$ represents a hydrogen atom and $R_2$ represents a 4-diethylamino-1-methylbutyl group or a 3-diethylaminomethyl-4-hydroxyphenyl group are substances possessing remarkable antimalarial properties and are known respectively under the names chloroquine and amodiaquin; the product of the general formula (I) in which the chlorine atom is in the 7-position, $R_1$ represents a hydrogen atom and $R_2$ represents a 2-carboxyphenyl group is an intermediate for the preparation of the dihydroxypropyl ester of N-(7-chloroquinol-4-yl)-anthranilic acid, known under the name glafenine, which is an analgesic and a powerful anti-inflammatory agent.

It is known, in particular from U.S. Pat. No. 2,653,940, to prepare chloroquine by condensing 4-diethylamino-1-methylbutylamine with 7-chloro-1,2,3,4-tetrahydroquinolin-4-one, the reaction preferably being carried out in the presence of air or nitrobenzene as an oxidising agent, or in the presence of palladium-on-charcoal as a dehydrogenation catalyst.

However, this condensation, which leads to a Schiff base as an intermediate and is associated with aromatisation, is accompanied by dechlorination. Thus, a mixture of chloroquinone and 4-(4-diethylamino-1-methylbutylamino)-quinoline is obtained.

It has now been found that the products of the general formula (I) can be obtained, with good yields and virtually free of dechlorinated product, by condensing an amine of the general formula:

in which $R_1$ and $R_2$ are as hereinbefore defined, with a chloro-1,2,3,4-tetrahydroquinolin-4-one of the general formula (II), this condensation being associated with aromatisation, the reaction being carried out in the presence of a ruthenium based catalyst on a support and preferably in the absence of oxygen; it is this finding which forms the subject of the present invention.

The reaction is preferably carried out using a catalyst consisting of ruthenium-on-charcoal or ruthenium-on-alumina, and in an excess of amine of the general formula (III), which can be used as a solvent, at a temperature between 100° and 200° C.

It is also possible to carry out the reaction in an organic solvent such as chlorobenzene or anisole, one or other of the reagents being used in slight excess, at the boiling point of the solvent or at a higher temperature, under pressure, and the water formed during the reaction optionally being separated off by azeotropic distillation.

The catalyst preferably contains about 5% by weight of metal and it is used in an amount such that the metal represents from 0.01 to 0.0001 gram atom per mol of reagent used, i.e. per mol of quinolin-4-one of the general formula (II) or per mol of amine of the general formula (III), depending on whether the quinoline of general formula (II) or the amine of the general formula (III) is used in excess.

It can be advantageous to carry out the reaction in the presence of halide ions and more particularly of iodide ions.

In general, an acid addition salt (preferably a hydrohalide) of the amine of general formula (III) is used.

By carrying out the process according to the invention, it is possible to obtain a product of the general formula (I) containing only a small proportion of dechlorinated product.

The proportion of dechlorinated product obtained, relative to the 1,2,3,4-tetrahydroquinolin-4-one of the general formula (II) converted, is generally less than 8% and, depending on the quality of the amine of the general formula (III) used, this proportion can be less than 1%.

The products of the general formula (I) can be separated from the reaction mixture and purified by applying customary methods such as crystallisation or chromatography.

The chloro-1,2,3,4-tetrahydroquinolin-4-one of the general formula (II) used as the starting material can advantageously be prepared by, for example, cyclising a 3-chloro-anilinopropionic acid by means of a mixture of hydrofluoric acid and boron trifluoride.

The 3-chloroanilinopropionic acid can be obtained by reacting excess chloroaniline with acrylic acid. The reaction is carried out in water at a temperature between 70° and 100° C. The reaction time is generally between 1 and 4 hours.

The following Examples, which are given without implying a limitation, show how the invention can be put into practice.

EXAMPLE 1

The following are introduced into a 50 cc round-bottomed flask fitted with a magnetic stirrer, a distillation column and a condenser:

| | |
|---|---|
| catalyst: composed of 48% by weight of ruthenium-on-charcoal and 54% of water [proportion of ruthenium in the dry catalyst: 5% (w/w)] | 97.3 mg |
| 7-chloro-1,2,3,4-tetrahydro-quinolin-4-one | 4.549 g |
| 1-diethylamino-4-aminopentane | 3.2655 g |
| 1-diethylamino-4-aminopentane dihydroiodide | 47.2 mg |
| anisole | 25 cc |

The outlet of the condenser is connected to a gasometer which makes it possible to measure the volume of gas evolved during the reaction. The reaction mixture is heated to the reflux temperature in 16 minutes. The temperature of the mixture is then kept constant and equal to 157° C. throughout the operation. The vapours are condensed at the top of the column and the heterogeneous distillate is decanted; the solvent is recycled continuously.

After a heating time of 5 hours, the volume of gas evolved is 435 cc.

The mixture is cooled, the catalyst is filtered off and the organic phase is washed with 1 N aqueous sodium hydroxide solution in order to free the amines present in salt form.

The organic solution thus obtained is examined by gas phase chromatography. The following results are obtained:

7-chloro-1,2,3,4-tetrahydroquinolin-4-one: 7.037 millimols for an amount of 25.063 millimols introduced at the start, i.e. a degree of conversion of 71.9%, 1-diethylamino-4-aminopentane: 1.518 millimols for a total initial amount of 19.882+0.114=19.996 millimols, i.e. a degree of conversion of 92.4%, chloroquine: 17.8 millimols, representing a yield (determined) of 99% relative to the 7-chloro-1,2,3,4-tetrahydroquinolin-4-one converted, and of 96.3% relative to the 1-diethylamino-4-aminopentane converted, and 4-(4-diethylamino-1-methylbutylamino)-quinoline: 0.08 millimol, which corresponds to a yield of 0.45% relative to the 7-chloro-1,2,3,4-tetrahydroquinolin-4-one converted.

The starting 7-chloro-1,2,3,4-tetrahydroquinolin-4-one can be prepared in the following manner:

3-m-Chloroanilinopropionic acid (94.5% pure) (10 g) is introduced into a stainless steel reactor containing liquid hydrofluoric acid (50 g) cooled to 5° C. The solution is saturated with gaseous boron trifluoride. For this purpose, the contents of the reactor are kept at 20° C. and then saturated with gaseous boron trifluoride under a pressure of 12 bars for 1 hour. The reactor is subsequently closed and then heated at 80° C. for 20 hours.

The pressure initially rises to 20 bars and then falls progressively until it stabilises at about 16 bars. The reactor is subsequently cooled to 10° C. and then opened so as to allow the boron trifluoride to escape.

The reddish liquid obtained is poured into a mixture of water and ice. After extraction with chloroform (3×100 cc), the organic layer is washed with water (several times 100 cc) until the pH of the washings is between 3 and 4, and is then dried over sodium sulphate. After filtration and concentration to dryness under reduced pressure (10 mm Hg; 1.33 kPa), crystalline 7-chloro-1,2,3,4-tetrahydroquinolin-4-one (9 g) is obtained, the purity of which is 94.5% as determined by gas phase chromatography.

The degree of conversion is 100% and the yield relative to the 3-m-chloroanilinopropionic acid is 99%.

The proportion of the 5-chloro isomer is about 0.7% as determined by gas phase chromatography.

The starting 3-m-chloroanilinopropionic acid can be prepared in the following manner:

A solution of acrylic acid (72.05 g) in water (100 cc) is added in the course of 10 minutes to a mixture of m-chloroaniline (510.3 g) and water (150 cc), kept under an argon atmosphere and stirred at 80° C. The reaction mixture consists of two phases and is kept at 80° C. for 3 hours, whilst stirring, and then cooled to 20° C. After settling, the aqueous phase (upper layer) is removed. A 2.6 N aqueous solution of sodium hydroxide (423 cc) is added to the organic phase, whilst stirring and keeping the temperature at 20° C. After settling, the organic phase, consisting of m-chloroaniline (303 g), is separated off. The aqueous phase (850 cc) is extracted with diethyl ether (6×450 cc in succession).

The aqueous phase, from which the ether is removed by evaporation under reduced pressure (20 mm Hg, 2.7 kPa), is acidified by adding 50% (by weight) sulphuric acid (105 g). The final pH is 3.5 (isoelectric point). The temperature increases from 22° to 33° C. and the mixture is then heated to 40° C. After settling, the following are separated off:

a lower organic phase (208.8 g) consisting of molten 3m-chloroanilinopropionic acid saturated with water (8.6% of water), and an upper aqueous phase (601 g) containing m-chloroanilinopropionic acid (2.28 g) and sodium sulphate (156 g).

The organic phase is heated for 1 hour at 80° C. under reduced pressure (20 mm Hg; 2.7 kPa). This yields a product (195.4 g) containing 94% of 3-m-chloroanilinopropionic acid and 2.3% of water.

The 1-diethylamino-4-aminopentane used as a starting material, the purity of which is more than 95%, is obtained after distillation, under a pressure of 30 mm Hg (4 kPa), of the reaction product of 5-diethylaminopentan-2-one with ammonia and hydrogen. The 5-diethylaminopentan-2-one can be obtained by reacting 1-diethylamino-2-chloroethane with sodated ethyl acetylacetate.

EXAMPLE 2

The procedure of Example 1 is followed, but a pre-reduced catalyst is used.

The catalyst (5% ruthenium-on-charcoal containing 57% of water and 43% of dry catalyst) (98.8 mg, i.e. 0.021 mg atom of ruthenium) is introduced into the flask. It is heated to 100° C. and a stream of hydrogen is then passed for 1 hour. It is cooled and the following are then introduced into the round-bottomed flask:

| | |
|---|---|
| 7-chloro-1,2,3,4-tetrahydro-quinolin-4-one | 4.5617 g (25.133 millimols) |

| | |
|---|---|
| 1-diethylamino-4-amino-pentane (obtained under the conditions described in Example 1) | 3.307 g (20.135 millimols) |
| 1-diethylamino-4-amino-pentane dihydroiodide | 48.7 mg (0.117 millimol) |
| anisole | 25 cc |

The procedure of Example 1 is followed. After a heating time of 5 hours under reflux, the volume of gas evolved is 447 cc.

After the catalyst has been filtered off and the organic phase washed with an N solution of sodium hydroxide, the following are determined by gas chromatography:

7-chloro-1,2,3,4-tetrahydroquinolin-4-one: 6.875 millimols, which corresponds to a degree of conversion of 72.6%, 1-diethylamino-4-aminopentane: 1.769 millimols, i.e. a degree of conversion of 91.3%, chloroquine: 17.904 millimols, i.e. a yield of 98.05% relative to the 7-chloro-1,2,3,4-tetrahydroquinolin-4-one converted, and a yield of 96.86% relative to the 1-diethylamino-4-amino-pentane converted, and 4-(4-diethylamino-1-methylbutylamino)-quinoline: 0.08 millimol, which represents a yield of 0.43% relative to the 7-chloro-1,2,3,4-tetrahydroquinolin-4-one converted.

EXAMPLE 3

The procedure of Example 1 is followed, but the following products are used:

| | |
|---|---|
| catalyst (5% (w/w) ruthenium on-charcoal containing 50% of water and 50% of dry catalyst) | 154.6 mg (0.0382 mg atom) |
| 7-chloro-1,2,3,4-tetrahydro-quinolin-4-one | 961.5 mg (5.297 millimols) |
| 1-diethylamino-4-amino-pentane (obtained under the conditions described in Example 1) | 642.2 mg (3.910 millimols) |
| 1-diethylamino-4-amino-pentane dihydrochloride | 51.7 mg (0.224 millimol) |
| chlorobenzene | 12 cc |

The mixture is heated under reflux for 4 hours 30 minutes, the temperature of the reaction mixture being 136° C.

After the catalyst has been filtered off and the organic phase washed with sodium hydroxide solution under the conditions described in Example 1, the following are determined by gas phase chromatography:

7-chloro-1,2,3,4-tetrahydroquinolin-4-one: 1.216 millimols, i.e. a degree of conversion of 77%, 1-diethylamino-4-aminopentane: 0.115 millimol, i.e. a degree of conversion of 97.2%, chloroquine: 3.665 millimols, i.e. a yield of 90% relative to the 7-chloro-1,2,3,4-tetrahydroquinolinone converted, and a yield of 91.2% relative to the 1-diethylamino-4-aminopentane converted, and 4-(4-diethylamino-1-methylbutylamino)-quinoline: estimated yield of 3.5% relative to the 7-chloro-1,2,3,4-tetrahydroquinolin-4-one converted.

EXAMPLE 4

The procedure of Example 1 is followed, but using the following:

| | |
|---|---|
| catalyst (5% (w/w) ruthenium-on-charcoal containing 50% of water and 50% of dry catalyst) | 757.8 mg (0.187 mg atom) |
| 7-chloro-1,2,3,4-tetrahydro-quinolin-4-one | 4.8199 g (26.556 millimols) |
| 1-diethylamino-4-aminopentane (obtained under the conditions described in Example 1) | 3.2465 g (19.767 millimols) |
| 1-diethylamino-4-aminopentane dihydrochloride | 259.1 mg (1.121 millimols) |
| 1-diethylamino-4-aminopentane dihydroiodide | 41 mg (0.099 millimol) |
| chlorobenzene | 25 cc |

The mixture is heated under reflux for 4 hours 50 minutes; the volume of gas evolved is 470 cc.

The following are determined by chromatographic analysis:

7-chloro-1,2,3,4-tetrahydroquinolin-4-one: 6.418 millimols, i.e. a degree of conversion of 75.8%, 1-diethylamino-4-aminopentane: 1.391 millimols, i.e. a degree of conversion of 93.4%, chloroquine: 19.116 millimols, i.e. a yield of 94.9% relative to the 7-chloro-1,2,3,4-tetrahydroquinolin-4-one converted, and a yield of 97.5% relative to the 1-diethylamino-4-amino-pentane converted, and 4-(4-diethylamino-1-methylbutylamino)-quinoline: estimated yield of 1% relative to the 7-chloro-1,2,3,4-tetrahydroquinolin-4-one converted.

EXAMPLE 5

The procedure of Example 1 is followed, but using the following:

| | |
|---|---|
| catalyst: ruthenium-on-charcoal containing 2.15% w/w of ruthenium metal | 98.5 mg (0.021 mg atom) |
| 7-chloro-1,2,3,4-tetrahydro-quinolin-4-one | 3.6007 g (19.84 millimols) |
| 1-diethylamino-4-aminopentane obtained under the conditions described in Example 1 and having a purity of 96.2% | 4.118 g (25.03 millimols) |
| 1-diethylamino-4-methylpentane dihydroiodide | 28.2 mg (0.064 millimol) |
| anisole | 15 cc |

The procedure of Example 1 is followed. After heating under reflux for 5 hours 30 minutes, the reaction mixture is cooled. The catalyst is filtered off. The organic phase is washed with an N aqueous solution of sodium hydroxide. The following are then determined in the organic phase by gas phase chromatography:

| | |
|---|---|
| 7-chloro-1,2,3,4-tetrahydro-quinolin-4-one (which corresponds to a degree of conversion of 90.2%) | 1.95 millimols |
| 1-diethylamino-4-aminopentane (which corresponds to a degree of conversion of 78.33%) | 5.437 millimols |
| chloroquine (i.e. a yield of 99.6% relative to the 7-chloro-1,2,3,4-tetrahydro-quinolin-4-one converted, and a yield of 90.7% relative to the 1-diethylamino-4-aminopentane converted) | 17.827 millimols |
| 4-(4-diethylamino-1-methyl-butylamino)-quinoline (i.e. a yield of 0.36% relative to the 7-chloro-1,2,3,4-tetrahydro- | 0.064 millimol | quinolin-4-one converted)

EXAMPLE 6

The procedure of Example 1 is followed, but using the following:

| | |
|---|---|
| catalyst: 5% (w/w) ruthenium-on-alumina | 42.9 mg (0.021 mg atom) |
| 7-chloro-1,2,3,4-tetrahydro-quinolin-4-one | 4.533 g (24.975 millimols) |
| 1-diethylamino-4-amino-pentane having a purity of 96.2% | 3.471 g (21.133 millimols) |
| 1-diethylamino-4-aminopentane dihydroiodide | 25.9 mg (0.059 millimol) |
| anisole | 25 cc |

The procedure of Example 1 is followed. After heating under reflux for 7 hours, the reaction mixture is cooled.

After the catalyst has been filtered off and the organic phase washed with an N aqueous solution of sodium hydroxide, the following are determined by gas phase chromatography:

| | |
|---|---|
| 7-chloro-1,2,3,4-tetrahydro-quinolin-4-one (which corresponds to a degree of conversion of 74.8%) | 6.301 millimols |
| 1-diethylamino-4-amino-pentane (which corresponds to a degree of conversion of 92.7%) | 1.551 millimols |
| chloroquine (i.e. a yield of 96.7% relative to the 7-chloro-1,2,3,4-tetrahydro-quinolin-4-one converted, or of 91.9% relative to the 1-diethylamino-4-amino-pentane converted) | 18.057 millimols |
| 4-(4-diethylamino-1-methylbutyl-amino)-quinoline (i.e. a yield of 1.37% relative to the 7-chloro-1,2,3,4-tetrahydro-quinolin-4-one converted) | 0.257 millimol |

EXAMPLE 7

The procedure of Example 1 is followed, but using the following:

| | |
|---|---|
| catalyst: ruthenium-on-charcoal containing 2.15% (w/w) of ruthenium metal | 98.7 mg (0.021 mg atom) |
| 7-chloro-1,2,3,4-tetrahydro-quinolin-4-one | 4.5734 g (25.197 millimols) |
| 1-diethylamino-4-amino-pentane | 3.4651 g (21.097 millimols) |
| 1-diethylamino-4-aminopentane dihydroiodide | 26.1 mg (0.057 millimol) |
| anisole | 21 cc |

The procedure of Example 1 is followed. After heating under reflux for 8 hours, the volume of gas evolved is 487 cc, measured at a temperature of the order of 20° C. After the reaction mixture has cooled, the catalyst is filtered off. The organic phase is washed with an N aqueous solution of sodium hydroxide and the following are then determined by gas phase chromatography:

| | |
|---|---|
| 7-chloro-1,2,3,4-tetrahydro-quinolin-4-one (i.e. a degree of conversion of 83.9%) | 4.047 millimols |
| 1-diethylamino-4-amino-pentane (i.e. a degree of conversion of 97.7%) | 0.484 millimol |
| chloroquine (i.e. a yield of 96.6% relative to the 7-chloro-1,2,3,4-tetrahydro-quinolin-4-one converted, or of 98.9% relative to the 1-diethylamino-4-amino-pentane converted) | 20.439 millimols |
| 4-(4-diethylamino-1-methyl-butylamino)-quinoline (i.e. a yield of 0.28% relative to the 7-chloro-1,2,3,4-tetrahydro-quinolin-4-one converted) | 0.06 millimol |

EXAMPLE 8

The procedure of Example 1 is followed, but using the following:

| | |
|---|---|
| catalyst: 5% (w/w) ruthenium-on-charcoal | 46.7 mg (0.023 mg atom) |
| 7-chloro-1,2,3,4-tetrahydro-quinolin-4-one | 4.4864 g (24.718 millimols) |
| aniline | 1.9155 g (20.597 millimols) |
| aniline hydrochloride | 29.9 mg (0.23 millimol) |
| anisole | 25 cc |

The procedure of Example 1 is followed. After heating under reflux for 5 hours, distillate (15 cc) is removed over a period of 30 minutes and the heating under reflux is then continued for a further 3 hours. During the second part of the reaction, the temperature of the reaction mixture under reflux is 170° C. The volume of gas evolved is 455 cc, measured at a temperature of the order of 20° C. A precipitate appears on cooling. This precipitate is filtered off and then taken up in hot ethanol. The catalyst is filtered off. The filtrate is concentrated to dryness. This yields a solid A (3.55 g).

The organic phase is washed with an N aqueous solution of sodium hydroxide and then with an N solution of hydrochloric acid. In the organic phase washed in this way, the following is determined by gas phase chromatography:

| | |
|---|---|
| 7-chloro-1,2,3,4-tetrahydro-quinolin-4-one (i.e. a degree of conversion of 82.3%) | 4.374 millimols |

The aqueous hydrochloric acid solution is rendered alkaline with an N aqueous solution of sodium hydroxide and is then extracted with diethyl ether. The following is determined in the ether phase by gas phase chromatography:

| | |
|---|---|
| aniline (i.e. a degree of conversion of 97.1%) | 0.604 millimol |

The ether phase is concentrated to dryness. The residue obtained and the solid A are combined and dissolved in hot ethanol. On cooling, a crystalline precipitate is obtained which is filtered off. This yields 4-anilino-7-chloroquinoline (2.475 g) melting at 209° C.

After concentration of the filtrate, a second fraction of 4-anilino-7-chloroquinoline (1.325 g), melting at 207° C., is obtained.

The isolated product is virtually pure as determined by thin layer chromatography and by gas phase chromatography.

The yield of 4-anilino-7-chloroquinoline isolated is 73.4% relative to the quinolin-4-one converted, and 73.8% relative to the aniline converted.

EXAMPLE 9

The procedure of Example 1 is followed, but using the following:

| | |
|---|---|
| catalyst: 5% (w/w) ruthenium-on-charcoal | 45.3 mg (0.022 mg atom) |
| 7-chloro-1,2,3,4-tetrahydro-quinolin-4-one | 4.5212 g (24.91 millimols) |
| anthranilic acid | 2.9668 g (21.655 millimols) |
| anisole | 15 cc |

The mixture is heated under reflux for 5 hours, whilst stirring.

During the reaction, a precipitate appears in the reaction mixture. After cooling, the precipitate is filtered off and is then taken up in hot acetic acid. The catalyst is then filtered off. After cooling, a light yellow crystalline precipitate is obtained which is filtered off. After recrystallization from methanol, 4-[(2-carboxyphenyl)-amino]-7-chloroquinoline (3.829 g), having a purity of 95.03%, is obtained.

In the filtrate obtained after the first filtration, the following is determined by gas phase chromatography:

| | |
|---|---|
| 7-chloro-1,2,3,4-tetrahydro-quinolin-4-one (which corresponds to a degree of conversion of 86.3%) | 3.406 millimols |

The 4-[(2-carboxyphenyl)-amino]-7-chloroquinoline is obtained with a yield of 56.7% relative to the quinolin-4-one converted.

EXAMPLE 10

The following are introduced into the apparatus described in Example 1:

| | |
|---|---|
| catalyst: 5% (w/w) ruthenium-on-charcoal | 49.3 mg (0.024 mg atom) |
| 7-chloro-1,2,3,4-tetrahydro-quinolin-4-one | 4.5398 g (25.012 millimols) |
| N—methylaniline | 2.3176 g (21.694 millimols) |
| N—methylaniline hydrochloride | 28.8 mg (0.2 millimol) |
| anisole | 15 cc |

The mixture is heated under reflux for 5 hours and distillate (5 cc) is then removed. The heating is continued for a further 2 hours 30 minutes. The volume of gas evolved is 477 cc.

After cooling, a precipitate forms which is filtered off and then taken up in an N aqueous solution of sodium hydroxide. The catalyst is filtered off. The organic filtrate from the first filtration is washed with the N aqueous sodium hydroxide solution which was used to take up the precipitate. After acidification of the aqueous phase to pH 6 and extraction with butanol, 7-chloro-4-hydroxyquinoline (1.43 g) is obtained.

The organic phase is then washed with N hydrochloric acid. The following is determined in the organic phase by gas phase chromatography:

| | |
|---|---|
| 7-chloro-1,2,3,4-tetrahydro-quinolin-4-one (which corresponds to a degree of conversion of 79.3%) | 5.175 millimols |

The acid aqueous solution is rendered alkaline by adding N sodium hydroxide solution and is then extracted with diethyl ether. The following is determined in this ether extract by vapour phase chromatography:

| | |
|---|---|
| N—methylaniline (which corresponds to a degree of conversion of 58.8%) | 9.013 millimols |

After the ether has been evaporated off, the residue obtained is recrystallised from hexane. This yields 4-(N-methyl-N-phenylamino)-7-chloroquinoline (2.117 g).

The yield is 40% relative to the quinolin-4-one converted, and 61% relative to the N-methylaniline converted.

EXAMPLE 11

The following are introduced into the apparatus described in Example 1:

| | |
|---|---|
| catalyst: 5% (w/w) ruthenium-on-charcoal | 48.9 mg (0.024 mg atom) |
| 7-chloro-1,2,3,4-tetrahydro-quinolin-4-one | 4.572 g (25.19 millimols) |
| di-(n-butyl)-amine | 17 cc |
| di-(n-butyl)-amine hydrochloride | 344.4 mg (2.08 millimols) |
| chlorobenzene | 2 cc |

The mixture is heated under reflux for 11 hours. After cooling, the catalyst is filtered off. The filtrate, to which chlorobenzene has been added, is washed with an N aqueous solution of sodium hydroxide. The organic phase is washed with an N solution of hydrochloric acid. The following is determined in the organic phase by gas phase chromatography:

| | |
|---|---|
| 7-chloro-1,2,3,4-tetrahydro-quinolin-4-one (which corresponds to a degree of conversion of 87.4%) | 3.17 millimols |

The hydrochloric acid solution is rendered alkaline by adding an N aqueous solution of sodium hydroxide and is then extracted with diethyl ether. After concentration of the ether phase under reduced pressure, an oil (4.73 g), consisting essentially of 4-N,N-dibutylamino-7-chloroquinoline, is obtained.

EXAMPLE 12

The following are introduced into the apparatus described in Example 1:

| | |
|---|---|
| catalyst: 5% (w/w) ruthenium-on-charcoal | 47.7 mg (0.023 mg atom) |
| 7-chloro-1,2,3,4-tetrahydro-quinolin-4-one | 4.454 g (24.54 millimols) |
| p-aminophenol | 2.2247 g (20.41 millimols) |
| p-aminophenol hydroiodide | 51.5 mg (0.022 millimol) |
| anisole | 25 cc |

The mixture is heated under reflux for 17 hours. After cooling, a precipitate forms which is filtered off and then dissolved in hot ethanol. The catalyst is then filtered off.

By adding hot water to the alcoholic filtrate, a pale yellow precipitate forms which is filtered off. This yields 4-(4-hydroxyphenyl)-amino-7-chloroquinoline (3.006 g) melting at 257° C.

By partial concentration of the filtrate, 4-(4-hydroxyphenyl)-amino-7-chloroquinoline (0.605 g), melting at 255° C., is obtained.

The anisole-containing solution produced by the first filtration is washed with a 2 N aqueous solution of sulphuric acid. The following is determined in the organic phase by gas phase chromatography:

| | |
|---|---|
| 7-chloro-1,2,3,4-tetrahydro-quinolin-4-one (which corresponds to a degree of conversion of 79.45%) | 5.043 millimols |

The aqueous phase is brought to pH 8. After concentration and extraction, p-aminophenol (3.685 millimols) is determined (which corresponds to a degree of conversion of 81.9%) and, after crystallisation from an aqueous-alcoholic medium, 4-(4-hydroxyphenyl)-amino-7-chloroquinoline (0.310 g), melting at 255° C., is isolated.

The yield of 4-(4-hydroxyphenyl)-amino-7-chloroquinoline is 74.35% relative to the 7-chloro-1,2,3,4-tetrahydroquinolin-4-one converted, and 86.6% relative to the p-aminophenol converted.

The 4-(4-hydroxyphenyl)-amino-7-chloroquinoline can be converted to amodiaquin in accordance with the method described by J. H. BURCKHACTER et al., J. Amer. Chem. Soc., 72, 1,024 (1950).

We claim:

1. A process for the preparation of a 4-amino-chloroquinoline of the formula:

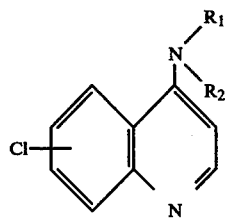

in which $R_1$ represents hydrogen or alkyl of 1 through 5 carbon atoms, and $R_2$ represents alkyl of 1 through 5 carbon atoms, alkyl of 1 through 5 carbon atoms substituted by a dialkylamino group of which each alkyl radical contains 1 through 4 carbon atoms, phenyl, or phenyl substituted by one or more radicals selected from carboxy and hydroxy and alkyl radicals of 1 through 4 carbon atoms optionally substituted by a dialkylamino group of which each alkyl radical contains 1 through 4 carbon atoms, which comprises carrying out the condensation of an amine of the general formula:

in which $R_1$ and $R_2$ are as hereinbefore defined, with a chloro-1,2,3,4-tetrahydroquinolin-4-one of the formula:

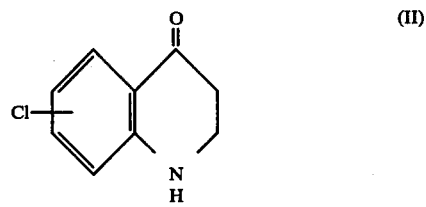

with aromatisation of the tetrahydroquinoline, the reaction being carried out in the presence of a ruthenium based catalyst on a support.

2. A process according to claim 1 in which the reaction between the amine and quinolin-4-one is carried out in the absence of oxygen.

3. A process according to claim 1 or 2 in which the condensation of the amine with the quinolin-4-one and aromatisation of the latter is carried out in the presence of ruthenium-on-charcoal or ruthenium-on-alumina.

4. A process according to claim 1 in which the reaction is effected using an excess of the amine reactant of formula (III) depicted in claim 1 as solvent medium.

5. A process according to claim 1 in which the reaction between the amine and the quinolin-4-one is effected in an organic solvent.

6. A process according to claim 4 in which the reaction is carried out at a temperature between 100° and 200° C.

7. A process according to claim 3 in which the reaction is carried out under a pressure greater than atmospheric.

8. A process according to claim 3 in which the water formed during the condensation reaction is removed by azeotropic distillation.

9. A process according to claim 1 wherein the condensation reaction between the amine and quinolin-4-one is carried out in the presence of halide ions.

10. A process according to claim 1 in which a hydrogen halide of the amine reactant of formula (III) depicted in claim 1 is present.

11. A process according to claim 1 in which 7-chloro-1,2,3,4-tetrahydroquinolin-4-one is reacted with 4-diethylamino-1-methylbutylamine, and chloroquine thus obtained is isolated.

* * * * *